United States Patent
Larsen

(10) Patent No.: US 10,782,306 B2
(45) Date of Patent: Sep. 22, 2020

(54) METHOD AND A SYSTEM FOR DETERMINATIONS OF CELL SUSPENSIONS

(71) Applicant: KONINKLIJKE PHILIPS N.V., Eindhoven (NL)

(72) Inventor: Niels Agersnap Larsen, Nivaa (DK)

(73) Assignee: KONINKLIJKE PHILIPS N.V., Eindhoven (NL)

(*) Notice: Subject to any disclaimer, the term of this patent is extended or adjusted under 35 U.S.C. 154(b) by 105 days.

(21) Appl. No.: 16/064,780

(22) PCT Filed: Dec. 22, 2016

(86) PCT No.: PCT/EP2016/082372
§ 371 (c)(1),
(2) Date: Jun. 21, 2018

(87) PCT Pub. No.: WO2017/109068
PCT Pub. Date: Jun. 29, 2017

(65) Prior Publication Data
US 2018/0372758 A1    Dec. 27, 2018

(30) Foreign Application Priority Data
Dec. 24, 2015    (EP) .................................... 15202725

(51) Int. Cl.
*G01N 33/49*    (2006.01)
*G01N 33/72*    (2006.01)
(Continued)

(52) U.S. Cl.
CPC ...... *G01N 33/721* (2013.01); *B01L 3/502707* (2013.01); *G01N 21/0303* (2013.01);
(Continued)

(58) Field of Classification Search
CPC combination set(s) only.
See application file for complete search history.

(56) References Cited

U.S. PATENT DOCUMENTS 4,790,640 A    12/1988    Nason
5,692,503 A    12/1997    Kuenstner
(Continued)

FOREIGN PATENT DOCUMENTS

JP    2007040814 A    2/2007
WO    199624876 A1    8/1996
(Continued)

OTHER PUBLICATIONS

Nam, Jeong-Hun et al "Comparison of Light-Transmission and backscattering methods in the Measurement of Red Blood Cell Aggregation", Journal of Biomiedical Optics, vol. 15, No. 2, 2010.

*Primary Examiner* — Omar S Ismail
(74) *Attorney, Agent, or Firm* — Sherry Austin

(57) ABSTRACT

The invention relates to a method of determining a concentration of a substance in a cell suspension, said method comprising the following steps: —determining the concentration of the substance by: —using the results of absorption measurements performed at n local sample volumes contained at different average chamber heights of a chamber arrangement comprising the cell suspension and local substance concentration in said respective local sample volumes determined based on said respective absorption measurements; —using a substance concentration model comprising local substance concentration as a function of chamber height, and—determining the substance concentration as the infinite chamber height substance concentration using said substance concentration model and the determined local substance concentrations, wherein n is at least 2, such as at least 3, such as at least 4, wherein, optionally, the cell suspension is whole blood and the substance is Hb and wherein the method further comprises determining cRBC based on the determined Hb concentration and a determined (Continued)

Non-overlapping RBC (red)    Overlapping RBCs (blue)

Mean Corpuscular Hemoglobin (MCH). The invention also relates to a system for executing the method.

12 Claims, 10 Drawing Sheets

(51) Int. Cl.
*B01L 3/00* (2006.01)
*G01N 21/03* (2006.01)

(52) U.S. Cl.
CPC ........ *G01N 33/49* (2013.01); *B01L 2200/148* (2013.01); *B01L 2300/0816* (2013.01); *B01L 2400/0406* (2013.01); *G01N 2021/0378* (2013.01); *G01N 2021/0392* (2013.01); *G01N 2201/066* (2013.01)

(56) References Cited

U.S. PATENT DOCUMENTS

| | | | |
|---|---|---|---|
| 5,773,301 A | 6/1998 | Werner | |
| 5,870,053 A | 2/1999 | Chamouard | |
| 5,898,487 A | 4/1999 | Hage | |
| 6,180,314 B1 | 1/2001 | Berndt | |
| 6,203,197 B1 | 3/2001 | Peter | |
| 6,350,613 B1 | 2/2002 | Levine | |
| 6,358,475 B1 | 3/2002 | Berndt | |
| 6,387,325 B1 | 5/2002 | Keusch | |
| 6,555,387 B1 | 4/2003 | Berndt | |
| 6,638,769 B2 | 10/2003 | Erikson | |
| 6,831,733 B2 | 12/2004 | Petterson | |
| 7,773,901 B2 | 8/2010 | Cho | |
| 7,782,447 B2 | 8/2010 | Lindberg | |
| 7,850,916 B2 | 12/2010 | Wardlaw | |
| 7,892,850 B2 | 2/2011 | Biwa | |
| 7,903,241 B2 | 3/2011 | Hill | |
| 7,929,121 B2 * | 4/2011 | Wardlaw | G01N 15/1475 356/39 |
| 8,077,296 B2 | 12/2011 | Lalpuria | |
| 8,310,695 B2 | 11/2012 | Back | |
| 8,472,693 B2 | 6/2013 | Davis | |
| 8,638,427 B2 | 1/2014 | Lalpuria | |
| 8,699,777 B2 | 4/2014 | Caillat | |
| 8,781,230 B2 | 7/2014 | Shieh | |
| 8,837,803 B2 | 9/2014 | Wang | |
| 8,906,308 B2 | 12/2014 | Garrett | |
| 2009/0238438 A1 * | 9/2009 | Wardlaw | G06T 7/0012 382/134 |
| 2011/0084033 A1 | 4/2011 | Villarreal | |
| 2011/0151502 A1 | 6/2011 | Kendall | |
| 2011/0159530 A1 | 6/2011 | Pass | |
| 2011/0256573 A1 * | 10/2011 | Davis | G01N 15/1475 435/29 |
| 2013/0045535 A1 * | 2/2013 | Soen | C12M 23/12 435/395 |
| 2013/0078668 A1 | 3/2013 | Levine | |
| 2014/0334712 A1 * | 11/2014 | Unfricht | G01N 21/5907 382/134 |
| 2015/0002834 A1 * | 1/2015 | Fine | G01N 1/28 356/36 |
| 2015/0029492 A1 | 1/2015 | Mpock | |
| 2015/0093760 A1 | 4/2015 | Kim | |
| 2015/0182588 A1 * | 7/2015 | Kahvejian | A61K 38/1774 424/1.69 |
| 2018/0135012 A1 * | 5/2018 | Mata-Fink | C07K 14/47 |

FOREIGN PATENT DOCUMENTS

| | | |
|---|---|---|
| WO | 199945365 A1 | 9/1999 |
| WO | 2006031095 A1 | 3/2006 |
| WO | 2007129948 A1 | 11/2007 |
| WO | 2010071430 A1 | 6/2010 |
| WO | 2015176744 A1 | 11/2015 |

* cited by examiner

Non-overlapping RBC (red)  Overlapping RBCs (blue)

METHOD AND A SYSTEM FOR DETERMINATIONS OF CELL SUSPENSIONS

CROSS-REFERENCE TO PRIOR APPLICATIONS

This application is the U.S. National Phase application under 35 U.S.C. § 371 of International Application No. PCT/EP2016/082372, filed on Dec. 22, 2016, which claims the benefit of European Patent Application No. 15202725.6, filed on Dec. 24, 2015. These applications are hereby incorporated by reference herein.

FIELD OF THE INVENTION

The invention generally relates to determination of a concentration of a substance in a cell suspension and in particular for determining hemoglobin concentration (cHb) in a whole blood sample. The invention also comprises a system for determining cell concentration in a cell suspension, in particular for determination of hemoglobin concentration (cHb) in a whole blood sample.

BACKGROUND OF THE INVENTION

Cell analysis methods, such as blood analysis methods are standard tools within the diagnostic area and there are many different methods and systems available to the users.

Accurate measurement of cell concentration in a biological sample is important in a variety of medical fields. For example, the concentration of hemoglobin (Hb) in blood or the concentration of sperm cell or of leukocytes in semen are used as diagnostic indicators.

An often used method of determining a cell concentration or a concentration of a substance in a cell suspension is a method comprising counting of the cells, e.g. using a flow cytometer. By know the flow rate the concentration may be calculated.

Many of the traditional blood analysis methods require separating of blood parts such as red blood cells or white blood cells, dilution and/or addition of expensive reagents.

Optical analysis methods have been found to be very advantageous, since such methods often are relatively fast. However, still many analysis methods require a time requiring sample preparation e.g. smear preparation.

US2011151502 describes a method for counting blood cells in a sample of whole blood. comprising: (a) providing a sample of whole blood; (b) depositing the sample of whole blood onto a slide, (c) employing a spreader to create a blood smear; (d) allowing the blood smear to dry on the slide; (e) measuring absorption or reflectance of light attributable to the hemoglobin in the red blood cells in the blood smear on the slide; (f) recording a magnified two-dimensional digital image of the area of analysis identified by the measurement in step (e) as being of suitable thickness for analysis; and (g) collecting, analyzing, and storing data from the magnified two-dimensional digital image.

Blood analysis directly on whole blood samples has also been suggested. US2015029492 describes a method for determining total hemoglobin concentration in a blood sample comprising spectrophotometric analysis of a blood sample at two wavelengths and determining a ratio of the detected radiation at a first wavelength to the detected radiation at a second wavelength; and determining a concentration of total hemoglobin in the blood sample based on the ratio. The sample is exposed to light at a plurality of wavelengths. Absorbance, transmission or reflectance measurements are made and the ratio of the measurements at two wavelengths indicates the amount of total hemoglobin.

However reflectance measurements tend to result in high uncertainty due to scattering effects and since the detected thickness layer of the sample is not well defined.

Optical detection using absorbance or transmission gives rise to another problem. In order to have sufficient transmission of a wavelength which is absorbable by hemoglobin through a layer of whole blood, the layer must be very thin or dilution of the sample is required.

However using thin layers requires a simple handling, which can be achieved by using microfluidic devices. Thin layers of fluid flowed into a in a microfluidic device will result in a change of particle concentration relatively to the original fluid sample due to the Segré-Silberberg effect. The Segré-Silberberg effect result in the concentration of particles flowing in laminar flow in a tube being accumulated at a small distance to the wall due to the parabolic nature of the laminar velocity profile in the flow which produces a shear-induced inertial lift force that drives particles towards the channel walls. As particles migrate closer to the channel walls, the flow around the particle induces a pressure increase between the particle and the wall which prevents particles from moving closer. Since the flow closer to the wall is slower than further from the wall, the concentration of particles in a liquid filled into a chamber of a flow cell with a small height will be reduced compared to the original particle concentration of the liquid prior to be filled into the flow cell. Determining the Hb concentration in a low thickness layer of blood e.g. 30 µm or less will therefore not give the correct result for the blood sample.

A method of avoiding this Segré-Silberberg effect is disclosed in WO2006031095. Here a special chamber with a relatively low height is provided with laminar flow disturbers to ensure that the chamber can be filled without triggering the Segré-Silberberg effect.

WO2010071430 describes another micro fluidic device which has been designed to avoid any concentration changes caused by the Segré-Silberberg effect. This micro-fluidic device including a base element, a cover element with an opened condition and a closed condition relative to the base element, a fluid chamber with a well-defined and fixed height, bounded by the base element and the cover element when the cover element is in the closed condition. Thereby the chamber can be filled without triggering the Segré-Silberberg effect.

SUMMARY OF THE INVENTION

It is an object of the invention to provide a method and a system for determining a concentration of a substance in a cell suspension which method and system are relatively simple and may be used even where the concentration of the substance is relatively high and without requiring dilution of the cell suspension.

It is a further object of the invention to provide a method and a system for determining a concentration of a substance in a cell suspension which method and system are fast to use and where a very accurate concentration determination may be obtained.

In an embodiment it is an object of the invention to provide a method and a system for determining hemoglobin concentration (cHb) in a whole blood sample where the determination is relatively fast and has a high accuracy.

In an embodiment it is an object of the invention to provide a method and a system for determining hemoglobin concentration (cHb) without requiring expensive additive or dilution of the blood sample.

In an embodiment it is an object of the invention to provide a method and a system for determining hemoglobin concentration (cHb) which is very cost effective in particular with respect to workload.

These and other objects have been solved by the invention or embodiments thereof as defined in the claims and as described herein below.

It has been found that the invention or embodiments thereof have a number of additional advantages which will be clear to the skilled person from the following description.

It should be emphasized that the term "comprises/comprising" as well as "including/included" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Reference made to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the skilled person will understand that particular features, structures, or characteristics may be combined in any suitable manner within the scope of the invention as defined by the claims.

The term "substantially" should herein be taken to mean that ordinary product variances and tolerances are included.

Thanks to the invention a very simple and fast method for determining a concentration of a substance in a cell suspension has now been provided.

The method comprises:
determining the concentration of the substance by:
using the results of absorption measurements performed at n local sample volumes contained at different average chamber heights of a chamber arrangement comprising the cell suspension and local substance concentration in said respective local sample volumes determined based on said respective absorption measurements;
using a substance concentration model comprising local substance concentration as a function of chamber height, and
determining the substance concentration as the infinite chamber height substance concentration using said substance concentration model and the determined local substance concentrations, wherein n is at least 2, such as at least 3, such as at least 4.

Another embodiment of the method comprises:
flowing the cell suspension into a chamber arrangement
performing absorption measurements of n local sample volumes contained at different average chamber heights of the chamber arrangement
determining the local substance concentration in the respective local sample volumes based on the respective absorption measurements,
generating a substance concentration model comprising local substance concentration as a function of chamber height, and
determining the substance concentration as the infinite chamber height substance concentration using the substance concentration model.

The number of local sample volumes at different average heights is at least 2, but advantageously the number is higher such as at least 3 or preferably at least 5. For most determination the number n of local sample volumes contained at different average chamber heights is from 2-10.

It should be understood that the chamber arrangement may comprise 1 or more chamber devices, such as up to n chamber devices. Consequently, the chamber arrangement may comprise, but is not limited to:

a plurality of chamber devices each comprising a sample volume of constant height, but for which the height is different for different chamber devices;

a single chamber device comprising a plurality of local sample volumes having different heights, wherein the height changes stepwise, continuously (e.g. a wedge-shaped sample volume), and/or stepwise-continuously (i.e. multiple, sloping sections with the angle of the slope carrying per section).

Any of the aforementioned arrangements, but also including a local sample volume of constant height, preferably a height such that the local sample volume comprise at least one area in which only a single layer of a particle type under investigation is present. For instance, when studying red blood cells such a preferred height is from about 2 μm to about 3.5 μm, such as from about 2.5 to about 3 μm.

The cells may be any kind of cells such as blood cells, sperm cells, tissue cells and bacteria. The cell suspension is advantageously whole blood. The substance of the cell suspension may be any kind of substance which can be optically detected by an absorption measurement. In an embodiment at least some of the cells are marked with an optically detectable marker. In an embodiment the substance to be detected is Hb. In an embodiment the substance is the cells of the cell suspension or a type of cells of the cell suspension.

In the following the invention is mainly described with reference to determination of haemoglobin Hb in blood. It should be understood that is merely a preferred example and that the method and system in a similar way is applicable for determining other substances in other dispersion is an equivalent or corresponding way.

In an embodiment a very simple and fast method for determining hemoglobin (Hb) concentration (cHb) in a whole blood sample is provided. The method of determining Hb concentration in a whole blood sample preferably comprises providing a chamber arrangement comprising n different chamber heights for holding local volumes, where the chamber arrangement is at least partially optically transparent for light of at least one preselected wavelength at the chamber heights flowing the blood sample into the chamber arrangement to provide local sample volumes at the different chamber heights performing absorption measurements of the local sample volumes contained at different chamber heights using a light source emitting light comprising at least the preselected wavelength determining the local Hb concentration in the respective local sample volumes generating a Hb concentration model comprising local Hb concentration as a function of chamber height, and determining the Hb concentration as the infinite height Hb concentration using the Hb concentration model.

The larger the number n of local sample volumes at different chamber heights the higher accuracy is in general obtained up to a certain level, but in practice 3 local sample volumes at different chamber heights has shown to be sufficient for most purposes when performing HB measurement on whole blood.

Where the number of local sample volumes at different chamber heights is 2 the height of at least one of the local sample volumes at different chamber heights should preferably be a local volume at a height above 20 μm, such as above 30 μm to ensure that the amount of blood in contact with the inner walls of the local sample volumes is not too high, such that the combined influence by the velocity difference over a cross section of the inflowing blood due to the Segré-Silberberg effect is not too large. Where the number n is larger than 2, this is not required.

Advantageously n is at least 2, such as at least 4, such as 2-10.

The terms "local volume" and "local sample volume" are used interchangeable unless otherwise specified. A local volume contained at a chamber height designate the volume on which the absorption measurements for that local sample volume is measured on.

The term "height" should be interpreted to mean the actual height where the height is uniform or to mean the average height where the height is not uniform. The term "average height" is identical to the actual height where it is uniform unless otherwise specified.

The chamber height at which a local volume is contained in the chamber arrangement may be a height section or a part of a height section.

The phrase "n local sample volumes contained at different average chamber heights of the chamber arrangement" means that the average height of the chamber arrangement for each of the n local volumes differs from each other. The method may comprise performing several local volumes at the same average height for increasing absorption measuring errors, e.g. by double or triple absorption measurements. Where the method comprises performing several local volumes at the same average height, the determination of the local substance concentration corresponding to this height (average height) are advantageously based on the average absorption determined of these local sample volumes at same average height.

The chamber height at which a local volume is contained in the chamber arrangement is determined as the average minimum height between a first and a second opposite inner surfaces of the chamber of the chamber arrangement. The first (e.g. top) and the second (e.g. bottom) opposite inner surfaces are the larger surfaces. Due to the relatively low height—i.e. preferably less than about 40 μm—the side surfaces connecting the first and the second opposite inner surfaces will be very narrow and any effect caused by the Segré-Silberberg effect by these side surfaces may be ignored, because the relatively amount of the local sample volumes which is near these side surface is insignificant.

The cells may be any kind of cells such as blood cells, sperm cells, tissue cells and bacteria. The cell suspension is advantageously whole blood. The substance of the cell suspension may be any kind of substance which can be optically detected by an absorption measurement. In an embodiment at least some of the cells are marked with an optically detectable marker. In an embodiment the substance to be detected is Hb. In an embodiment the substance is the cells of the cell suspension or a type of cells of the cell suspension. Where the cell suspension is whole blood, the sample used in the method is advantageously an undiluted whole blood sample.

Whole blood is defined as a venous, arterial or capillary blood sample in which concentrations and properties of cellular and extra-cellular constituents remain relatively unaltered when compared with their in vivo state.

In an embodiment the whole blood sample is free of any additives.

In an embodiment the whole blood sample comprises an anticoagulant. Anticoagulants are well known and includes for examples heparin, citrate or EDTA.

The chamber arrangement may in principle have any shape to provide the various average heights for the local sample volumes. In general it is desired that the chamber arrangement is shaped such that all the n local sample volumes at different chamber heights are filled from a common inlet, such that blood volumes from the same blood sample applied to the chamber arrangement will fill the various heights with the local sample volumes at different chamber heights. Advantageously the chamber arrangement has one single inlet for filling the local sample volumes at different chamber heights Examples of preferred chamber arrangements are shown in the appended figures. The chamber arrangement is advantageously in the form of one or more microfluidic devices.

In an embodiment the chamber arrangement is a single chamber and the cell suspension is supplied to the chamber arrangement to capillary load the local sample volumes to the chamber heights. Preferably the chamber heights are arranged along a common flow path of the chamber arrangement with gradually decreasing heights and preferably the flow path comprises at least 3 different chamber heights which differ from each other with at least about 2.5 μm.

In an embodiment the different local sample volumes at different chamber heights are arranged along a common flow path of the chamber arrangement, preferably with gradually decreasing heights.

Gradually decreasing heights may include continuously decreasing and/or downstream stepwise decreasing.

Term "downstream" means the direction from an inlet to a gas escape of a chamber (flow path) of the chamber arrangement. The gas escape arrangement may be a vent or similar such as it is known in the art of flow cells.

In an embodiment two or more of the n different local sample volumes at different chamber heights are arranged in separate flow chambers e.g. along the same flow paths of the chamber arrangement, such as separate flow paths with a common inlet for the blood sample and/or in side-by side arranged flow paths. The separate flow paths may advantageously be arranged in a side by side configuration allowing the image acquiring to be performed simultaneously for several local sample volumes at different chamber heights in a simple way.

An image should herein be interpreted to an array of light sensors, wherein each light sensor is represented by a pixel. Advantageously the image has a resolution of N×M pixels which is at least 1000 pixels, such as at least 10.000 pixels or even up to several mega pixels.

In an embodiment two or more of the n different local sample volumes at different chamber heights are arranged in a branched configuration e.g. comprising in downstream direction a first local sample volume at a chamber height with a first height h1, a second and a third local sample volumes at different chamber heights with respectively second and third heights h2, h3 branched off from the first path with local sample volume the height h1, wherein h1>h2>h3.

The local sample volumes at different chamber heights may have equal or different local volume size. In practice the local sample volumes at different chamber heights with larger heights will advantageously comprise a larger size of local volume than the local sample volumes at different chamber height with lower height.

The chamber or chambers comprising the heights for the local sample volume each have cross-sectional shape perpendicular to flow direction which in principle may have any shape. Advantageously the cross-sectional shape perpendicular to the flow direction when filling the chamber(s) is a regular shape which allows images to be acquired without undesired blurring due to irregularities resulting in irregular background noise, which may be difficult to account for.

Advantageously the cross-sectional shape perpendicular to flow direction of the chamber(s) of the chamber arrangement is round, oval, square or rectangular. Preferably the cross-sectional shape perpendicular to flow direction of the chamber(s) of the chamber arrangement is substantially rectangular with a substantially larger width than height, such as a width/height ratio of 2 or more such as at least about 5, such as at least about 100, such as at least about 500 or even higher.

The chamber arrangement can be of any material which is at least partially optically transparent for light of the preselected wavelength. It should be noted that the chamber arrangement may comprises non transparent material at other position than where the local sample volumes are contained.

Advantageously the chamber arrangement is of optical grade quality material, e.g. selected from glass or polymer, such as amorphous thermoplastic polymers and similar materials that can be used for producing high precision units e.g. by injection molding.

The chamber arrangement has one or more flow paths defined by it inner surfaces. The inner surfaces of the flow chamber arrangement may have any surface tension, e.g. the surface tension originating from the material of which the chamber arrangement is produced. It is desired that the surface tension or surface tensions (e.g. one surface tension in a top wall section and another surface tension in a bottom wall section of the respective local sample volumes at different chamber heights) defining each of the local sample volumes at different chamber heights are substantially identical from one local sample volumes at different chamber height to another.

The surface tension may be measured using a tensiometer, such as a SVT 20, Spinning drop video tensiometer marketed by DataPhysics Instruments GmbH. In this application the terms "surface tension" designate the macroscopic surface energy, i.e. it is directly proportional to the hydrophilic character of a surface measured by contact angle to water.

Advantageously at least a part of the inner surface of the chamber arrangement is hydrophilic.

It is generally desired that the maximal height of the local sample volumes at different chamber heights is selected such that the preselected wavelength is not completely absorbed.

It has been found to be highly advantageous to select the maximal height of the chamber heights for the local sample volumes in dependence on the depth of focus of the image acquisition device applied in the absorption measurements. Thereby a high quality absorption measurement may be obtained without requiring acquiring several images at different depths off the local volume the chamber heights. The image acquisition device may for example be a CCD camera or a CMOS detector.

In an embodiment the maximal height of the chamber heights is less than depth of focus of an image acquisition device applied in the absorption measurements. To ensure a good absorption measurement of the local volume it is generally desired that the maximal height of the chamber heights is about 40 µm or less, such as about 30 µm or less, such as about 25 µm or less, such as about 20 µm or less.

In an embodiment the chamber arrangement comprises at least 3 different chamber heights for local sample volumes, which respective chamber heights is in the interval from about 2 µm to about 25 µm. Preferred chamber heights are in the interval from about 2.5 µm to about 20 µm.

To ensure a high accuracy it is desired that the two or more and preferably at least 3 chamber heights containing local sample volumes has a substantially difference in height. Advantageously the chamber arrangement comprises at least 3 different chamber heights containing local sample volumes which chamber heights differ from each other in height with at least about 2.5 µm, such as at least about 3 µm.

Advantageously the blood sample is supplied to the chamber arrangement to fill the local sample volumes at different chamber heights via an inlet by capillary forces. Alternatively the blood sample may be filled into the ca be filled into the chamber arrangement to fill the local sample volumes at different chamber heights by forced flow e.g. by employing suction in a downstream end of a flow path of the chamber arrangement or by injecting the blood sample. For simple handling capillary filling is preferred.

Advantageously the blood sample and in particular the local volumes of the blood sample is held quiescently during the performance of the absorption measurements.

In an embodiment the chamber arrangement is at least partially optically transparent for light of at least one preselected wavelength to at least partially allow a light beam of the preselected wavelength passing through the chamber arrangement at the chamber heights. Preferably the absorption measurements of local sample volumes contained at the respective chamber heights comprises using a light source emitting light comprising at least the preselected wavelength.

The optical axis of the light emitted towards the local sample volumes may be substantially perpendicular to an upper surface of the chamber arrangement. In an embodiment the optical axis of the light emitted towards the local sample volumes has an angle to the upper surface of the chamber arrangement which is up to the critical angle (the angle where the light is reflected), such as up to about 60 degrees, such as up to about 30 degrees, preferably less than about 20 degrees.

Advantageously the preselected wavelength comprises a wavelength at an isobestic point of the substance, such as of Hb. Preferably the preselected wavelength comprises at least one of the wavelengths about 420 µm, about 530 µm and about 570 µm. By using a preselected wavelength comprises a wavelength at an isobestic point of Hb it is ensured that the absorption measurements of Hb is independent of the oxygen saturation. State of the Hb (oxyhemoglobin and deoxyhemoglobin).

The absorption measurements of local sample volumes contained in the chamber arrangement at different heights is performed using at least the preselected wavelength as light source.

In an embodiment the method comprises performing the absorption measurements of local sample volumes contained in the respective local sample volumes at different chamber heights using a light source emitting light comprising a range of wavelengths comprising the preselected wavelength, such as a range of wavelengths comprising at least about 5 µm, such as at least about 10 µm, such as at least about 25 µm, such as up to about 200 µm.

In an embodiment the method comprises performing two or more absorption measurements of each local sample volume contained at different chamber heights using a different wavelengths or ranges of wavelengths for each of the measurements. Thereby the Hb concentration determination may be even more accurate and/or the fraction of oxygenated/deoxygenated Hb may simultaneously be determined.

In an embodiment each of the absorption measurements comprises illuminating the local sample volume of the cell suspension at the chamber height from a first side of the chamber arrangement using the light source and recording transmitted light by acquiring at least one image on a second opposite side of the chamber arrangement, wherein the absorption measurements optionally are performed of local sample volumes at two or more of the chamber heights simultaneously.

The absorption measurements may be performed one by one of the respective local sample volumes at different chamber heights. Optionally absorption measurements are performed on two or more local sample volumes at different chamber heights with identical heights to improve result. For fast measurement it may be advantageous that two or more of the absorption measurements are performed simultaneously. The light source may advantageously emit the light in a direction substantially perpendicular to the direction of the height (or the shortest height where the height is not identical in the whole height section). In a variation the light source emits the light in a direction not perpendicular to the direction of the height (or the shortest height where the height is not identical in the whole height section), but for example with an angle of up to about 30 degrees to the direction of the height. In the latter embodiment the local sample volume of the height section is the volume which is illuminated by the light.

In an embodiment the determination of the local Hb concentration in each of the respective local sample volumes comprises image processing the acquired image or images of the local sample volumes at different chamber height in question to be normalized with respect to the background intensity. As a result the RBC free area is mapped to unity while RBCs are mapped to normalized intensities less than unity. Such normalization of the background illumination profile may be achieved by well-known methods.

In an embodiment the image processing comprises removing interference generated by free plasma Hb by applying a background normalization and correlating the total normalized light intensity of the acquired image of the local sample volumes at different chamber height to a local Hb concentration (i.e. the portion bounded to the red blood cells) at the height (z) in question.

In an embodiment the acquired image is converted to an Hb concentration map and enables quantization of RBC-free areas to ideally at a zero level while RBC populated areas are non-zero and originating from blood cell bound Hb.

The removal of interferences may advantageously comprise compensating for background intensity e.g. by determining a reference light intensity $I^{ref}$ or by calculation and/or by calibration;

$$cHb(z) = \frac{\gamma \cdot \sum_{ij \in \Theta} \ln\left(\frac{I_{ij}}{I_{ij}^{ref}}\right)}{LV(z)}$$

where ij indicates pixel location (i,j) of image $\Theta$, $I_{ij}$ is the measured light intensity of pixel ij, $I_{ij}^{ref}$ is the reference (background illumination) intensity of pixel ij, $\gamma$ is a constant which is calculated or determined by calibration, z is the chamber height containing local sample volume in question and LV (z) is the local volume at the chamber height with the height z defined on domain $\Theta$.

The generation of the Hb concentration model comprising local Hb concentration as a function of chamber height may be performed by using curve fitting software based on a number of plots.

In an embodiment the generation of the Hb concentration model comprising mapping the local Hb concentrations (LcHb) as a function of the height z (cHb(z)) and calculating a best fitting curve to the cHb(z) mapping and extrapolating the best fitting curve to a height for $z \to \infty$ and the Hb concentration. The best fitting curve may be calculated or it may be determined using standard curve fitting techniques such as least squares.

In an embodiment the method further comprises determining the Mean Corpuscular Hemoglobin (MCH). It has been found that the method of the invention is very suitable for determine MCH. The method for determining MCH comprises performing at least one absorption measurement of a local sample volume at a low chamber height of about 5 µm or less, and determining the MCH from the absorption measurement of the local sample volume at the low chamber height.

The local sample volume at the low chamber height may be one of the local sample volumes at different chamber heights used for the Hb determination or it may be an additional local sample volumes at a different and low chamber height of the chamber arrangement.

To ensure a high quality MCH determination it is desired that the low chamber height is sufficient low to ensure that at least some of the red blood cells are non-overlapping red blood cells. Preferably the low local sample volumes at different chamber height has a height of from about 2 µm to about 3.5 µm, such as from about 2.5 to about 3 µm.

In an embodiment the absorption measurement of the local sample volume at the low chamber height comprises acquiring at least one image and identifying image areas of a plurality of individual red blood cells and determining the absorbance of the identified areas and correlating the determined absorbance to the MCH. Preferably the method comprises counting the number of the plurality of individual red blood cells, determining the average absorbance of a blood cell and correlating the average absorbance of a blood cell to the MCH.

The Hb mHb mass of a single red blood cell may be determined a similar approach as described for determine cHb;

$$mHb = \gamma \cdot \sum_{ij \in \Omega} \ln\left(\frac{I_{ij}}{I_{ij}^{ref}}\right)$$

where Ω is set of pixel locations forming the red blood cell in the image. The Mean Corpuscular Hemoglobin (MCH) is thus the mean of mHb for a representative ensemble of red blood cells.

Depending on the condition of the patient from which the blood sample is drawn the red blood cell concentration of hemoglobin may vary more or less from cell to cell. To ensure a high quality MCH determination it is desired that an absorption of a relative large number of blood cells are used in the determination. Advantageously the plurality of individual red blood cells comprises at least about 1000 cells, such as at least about 2000 cells, such as least about 4000 cells, such as at least about 4200 cells, such as at least about 4400 cells.

Also it is advantageous that the local sample volume at least at the low chamber height has a 2D extension perpendicular to the height which is at least about 0.1 mm$^2$, such as at least about 0.2 mm$^2$, such as at least about 0.4 mm$^2$, such as at least about 0.3 mm$^2$.

The plurality of individual red blood cells is advantageously identified as non-overlapping red blood cells.

In an embodiment the method further comprises determining the concentration of red blood cells cRBC of the blood sample the method comprising correlating the determined Hb concentration to the MCH to thereby determining the cRBC.

The correlation of the determined Hb concentration to the MCH to determining the cRBC may simply be performed as follows:

$$cRBC = \frac{cHb}{MCH}$$

Advantageously the method further comprises determining the Hematocrit value (Hct), the method comprising deriving the Hct value empirically from the Hb concentration, such as $$Hct = 2.953 \frac{\% \, dL}{g} \cdot cHb$$

The method has been found also to be suitable for determining numerous of other blood parameters which may be found as derived parameter values. Preferred blood parameters include one or more of the following:

Mean Corpuscular volume (MCV),
Corpuscular Hemoglobin mass (mHb) distribution,
Red blood cell volume distribution (RDW–SD) or
Coefficient of variation for the RBC cell volume (RDW–SD).

The MCV may be determined as follows:

$$MCV = \frac{Hct}{cRBC} = \frac{Hct}{cHb} \cdot MCH = \frac{MCH}{MCHC} = 2.953 \frac{fL}{pg} \cdot MCH$$

where MCHC is the Mean Corpuscular Hemoglobin Concentration which becomes constant assuming the empirical relation described above.

The RDW-SD may be determined as follows:

$$RDW - SD =$$

-continued (RBC Hb mass distribution width presented as the standard deviation) ·

$$2953 \frac{fL}{pg}$$

The RDW-SD may be determined as follows:

RDW–SD=Coefficient of variation for the RBC cell Hb mass

The invention also comprises a system for determining hemoglobin (Hb) concentration (cHb) in a whole blood sample, such as a whole blood sample described above.

The system for determining a concentration of a substance in a cell suspension comprises a computer system programmed for causing the system to execute the method.

In an embodiment the system for determining a concentration of a substance in a cell suspension comprises a computer system programmed for generating a substance concentration model comprising local substance concentration as a function of chamber height, and determining the substance concentration as the infinite height substance concentration using the substance concentration model.

The system is preferably configured for performing the method of the invention and embodiments thereof as described above.

In an embodiment the system comprises
a chamber arrangement comprising n different chamber heights configured for being loaded by the cell suspension by flowing, and being at least partially optically transparent for at least one preselected wavelength to at least partially allow a light beam of the preselected wavelength passing through the chamber arrangement at the chamber heights,
a light source configured for emitting light comprising at least the preselected wavelength and being arranged to illuminate at least one a local sample volume at one of the n sample heights
an image acquisition device configured for acquire images of light passing through the local sample volume.

Advantageously the computer system further is programmed for processing images obtained by the image acquisition device of local sample volumes at n different heights to determine the local substance concentration in each of the respective local sample volumes. The integer "n" is advantageously as described for the method above.

In an embodiment where the system is suitable for determining hemoglobin (Hb) concentration (cHb) in a whole blood sample, the system advantageously comprises
a chamber arrangement comprising n different chamber heights for local sample volumes and where the chamber arrangement is at least partially optically transparent for at least one preselected wavelength to at least partially allow a light beam of the preselected wavelength passing through the chamber arrangement in the local sample volumes at different chamber heights,
a light source configured for emitting light comprising at least the preselected wavelength and being arranged to illuminate a sample area
an image acquisition device positioned to and configured for acquire light passing through the sample area
a sample holder adapted for holding the chamber arrangement in the sample area, and
a computer system.

The computer system is advantageously programmed for controlling the relative position of the chamber arrangement, the light source and the image acquisition device;

controlling the light source and the image acquisition device for illuminating the sample area and acquisition of images of light transmitted through the respective local sample volumes at different chamber heights;

acquiring images obtained by the image acquisition device; and processing the images to determine the Hb concentration of the blood sample.

The chamber arrangement is advantageously as described above.

The light source is advantageously a tunable light source such that the wavelength or the range of wavelengths is selectable by the user or the computer system may advantageously be programmed to select the wavelength or the range of wavelengths to comprise at least the selected wavelength.

The light source is configured for emitting light at least the preselected wavelength and being arranged to illuminate a sample area. Advantageously the computer system is programmed to ensure that the sample area into which the chamber arrangement is to be held by the sample holder is sufficiently illuminated for performing the absorption measurements.

The image acquisition device may in principle be any kind of image acquisition device, preferably having a high resolution such as a pixel resolution of as at least 10.000 pixels, such as at least 1 mega pixels. The image acquisition device preferably has a depth of view which is at least about the maximal chamber height.

The image acquisition device is positioned to and configured for acquire light passing through the sample area and is preferably arranged to acquiring images in focus of the local volume in the respective chamber heights either simultaneous or sequentially one by one or two by to or in any other configuration.

The computer system may comprise one single computer or a plurality of computers in data connection, wireless, by wire and/or via the internet.

The computer system advantageously comprises a storage medium comprising the computer program comprising instructions which when executed by the computer system cause the computer system to control the relative position of the chamber arrangement, the light source and the image acquisition device;

for perform absorption measurements of local blood volumes at different chamber heights by controlling acquisition of images of light transmitted through the respective local sample volumes; and process the images to determine the Hb concentration of the blood sample. Advantageously the processing of the images comprises determining the local Hb concentration in the respective local sample volumes generating a Hb concentration model comprising local Hb concentration as a function of chamber height, and determining the Hb concentration as the infinite height Hb concentration using the Hb concentration model.

The processing of each image for determination of the local Hb concentration in each of the respective local sample volumes comprises advantageously correcting the image for background noise, preferably by determining and/or monitoring background intensity ($I^{ref}$) e.g. as described in the method above.

In an embodiment the system is configured for determining the Hb concentration in whole blood, at least one of the chamber heights of the chamber arrangement is a low chamber height of about 5 μm or less and the computer system is programmed for performing absorption measurement by acquiring at least one image of a local blood volume at the low chamber height and for determining the MCH from the absorption measurement of the local blood volume at the low chamber height.

In an embodiment the absorption measurement of the local blood volume at the low chamber height comprises identifying image areas of a plurality of individual red blood cells and determining the absorbance of the identified areas and correlating the determined absorbance to the MCH, preferably the absorption measurement comprises counting the number of the plurality of individual red blood cells, determining the average absorbance of a blood cell and correlating the average absorbance of a blood cell to the MCH.

The method of determine MCH is described above.

The computer is advantageously programmed to identify the plurality of individual red blood cells as non-overlapping red blood cells.

In an embodiment the system further is configured for determining the concentration of red blood cells cRBC of the blood sample, the computer system being programmed to determining the concentration of red blood cells cRBC of the blood sample by correlating the determined Hb concentration to the MCH to thereby determining the cRBC.

In an embodiment the computer system further is programmed to determining the Hematocrit value (Hct) by a method comprising deriving the Hct value empirically from the Hb concentration e.g. using the method described above.

In an embodiment the computer system further comprises determining at least one of Mean Corpuscular volume (MCV), Corpuscular Hemoglobin mass (mHb) distribution, Red blood cell volume distribution (RDW–SD) or Coefficient of variation for the RBC cell volume (RDW–SD).

The applied methods may be as described above.

All features of the inventions including ranges and preferred ranges can be combined in various ways within the scope of the invention, unless there are specific reasons not to combine such features.

BRIEF DESCRIPTION OF THE DRAWINGS

Preferred embodiments of the invention will be further described with reference to the drawings.

FIG. 7 Middle shows the corresponding image of the top image mapped into hemoglobin 2D concentration.

FIG. 7 Bottom shows an example of RBC segmentation.

DETAILED DESCRIPTION OF THE EMBODIMENTS

Figure 9:
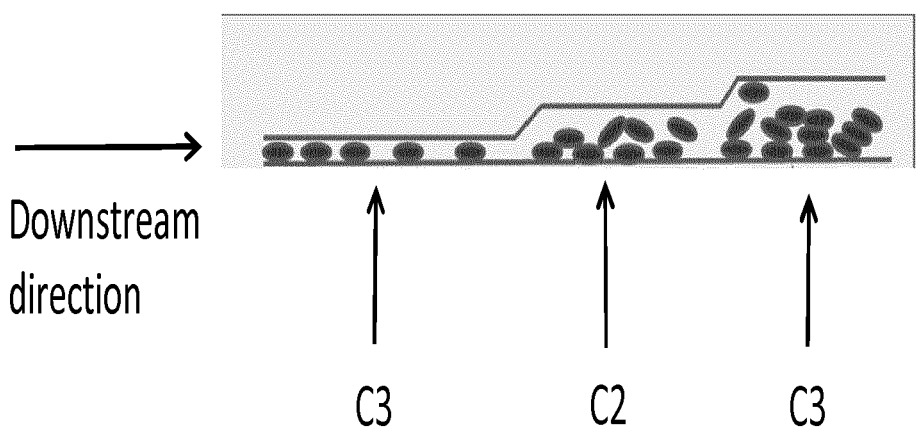

FIG. 9 is a cross sectional side view of a chamber arrangement into which a blood sample has been filled in downstream direction. In chamber height C1 (about 20 µm) the red blood cell are laying in several layers. In chamber height C2 (about 10 µm) the red blood cell are laying in about 3-4 layers, whereas in chamber height C3 (about 3 µm) the red blood cell are laying mainly in a single layer.

Figure 10:
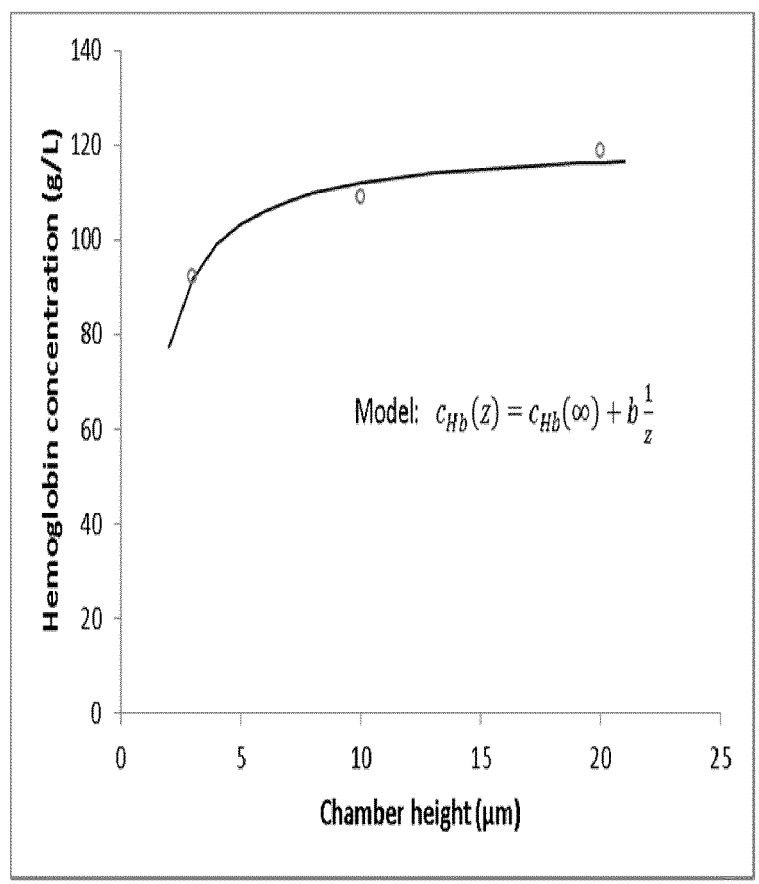

FIG. 10 is a plot showing the measured Hb concentration from the different chambers of height 3 µm, 10 µm and 20 µm. Due to the Segre-Silberberg effect the concentration is lower than the true concentration. The true value is 120 g/L and the fitted model predicts $c_{Hb}(\infty)=120.7$ g/L.

The figures are schematic and are not drawn to scale and may be simplified for clarity. Throughout, the same reference numerals are used for identical or corresponding parts.

Figure 1:
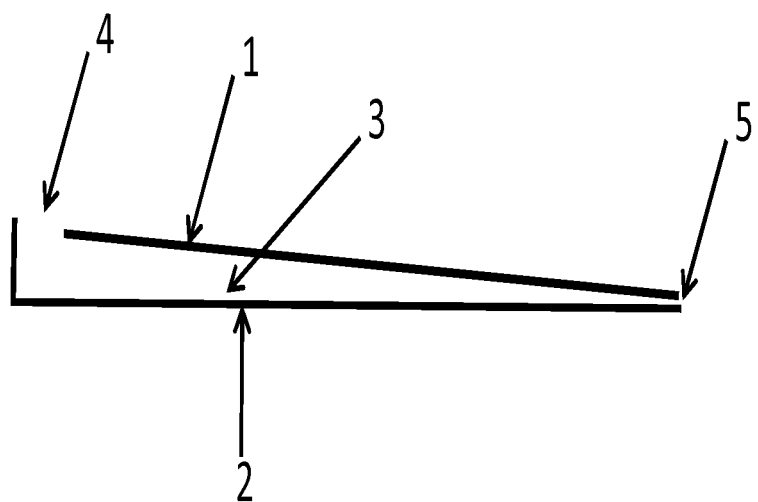
FIG. 1 is a schematic side view of an embodiment of a chamber arrangement with a chamber flow path continuously decreasing height in downstream direction suitable for use in the method and the system of the invention.

The chamber arrangement shown in FIG. 1 is a very simple construction comprising a top wall 1 and a bottom wall 2, without any side walls depicted in this figure, which together are defining a flow cell chamber 3 with continuously decreasing chamber height in downstream direction from an inlet 4 thereby providing an in principle infinite number of different chamber heights for local sample volumes. At the downstream end 5 the chamber arrangement comprises an escape opening allowing gas (air) to escape as the flow cell chamber 3 is filled with the blood sample. The escape opening is advantageously configured such that blood is not allowed to pass through the escape opening, thereby reducing any risk of spilling blood. The chamber arrangement is a disposal unit and is arranged for being disposed after a single use.

Figure 2:
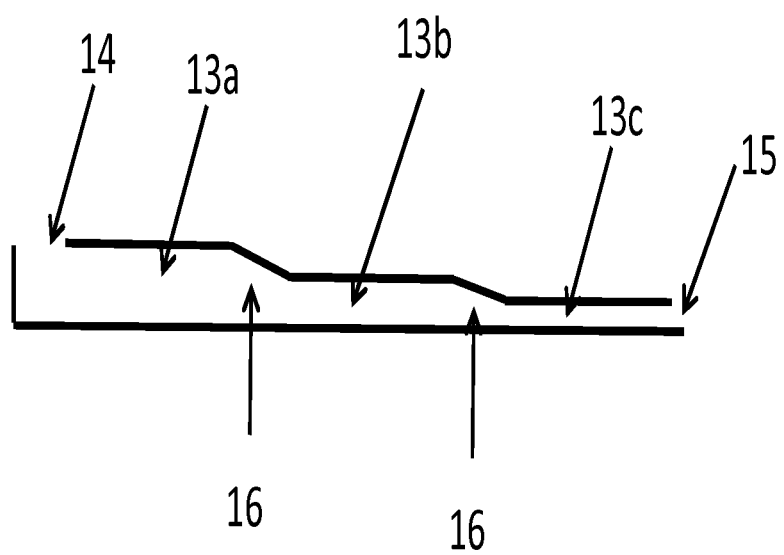
FIG. 2 is a schematic side view of an embodiment of a chamber arrangement with a chamber flow path with stepwise decreasing height in downstream direction suitable for use in the method and the system of the invention.

The chamber arrangement shown in FIG. 2 comprising a top wall and a bottom wall which together with not shown side walls are defining a flow cell chamber with 3 different sections for containing local sample volumes at different chamber heights 13*a*, 13*b*, 13*c* and 2 intermediate sections 16, which in principle could also be used as chamber heights for local sample volumes, but preferably are not. The intermediate sections may be long or short determined ion downstream direction and the lengths of the intermediate sections 16 are advantageously selected in view of making the chamber arrangement simple to produce with a high accuracy of chamber heights. The chamber heights 13*a*, 13*b*, 13*c* are decreasing in height in downstream direction from an inlet 14. In a not shown modification the chamber arrangement has 4, 5 or 6 ore even more different chamber heights arranged with decreasing heights in downstream direction. At the downstream end 15 the chamber arrangement comprises an escape opening allowing gas (air) to escape as the local sample volumes fills the chamber at the different chamber heights 13*a*, 13*b*, 13*c*.

Figure 3:
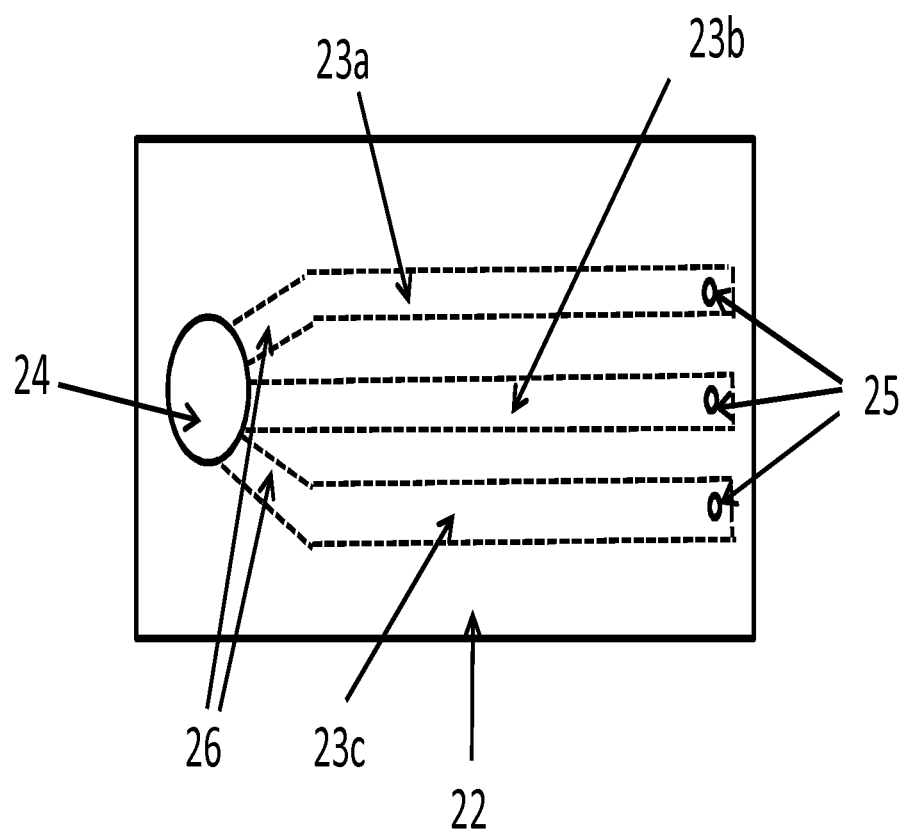
FIG. 3 is a schematic top view of an embodiment of a chamber arrangement with 3 separate flow path with different heights suitable for use in the method and the system of the invention.

The chamber arrangement 22 shown in FIG. 3 comprises a microfluidic chamber with 3 chamber heights 23*a*, 23*b*, 23*c* arranged parallel to each other and 2 intermediate sections 26 between an inlet 24 and the respective chamber heights 23*a* and 23*c* for guiding blood from the inlet 24 to these sections 23*a*, 23*c*. The intermediate sections 26 may also be used as chamber height for containing a local sample volume, but this is generally not preferred. The intermediate sections may be long or short determined ion downstream direction and the lengths of the intermediate sections 26 are advantageously selected in view of different chamber heights 23*a*, 23*b*, 23*c* for containing local sample volumes, have different heights, but are filled or tillable from the common inlet 24. At the downstream end the chamber heights 23*a*, 23*b*, 23*c* have each a gas escape opening 25 allowing gas (air) to escape as the local sample volumes are filled into the chamber heights 23*a*, 23*b*, 23*c*.

Figure 4:
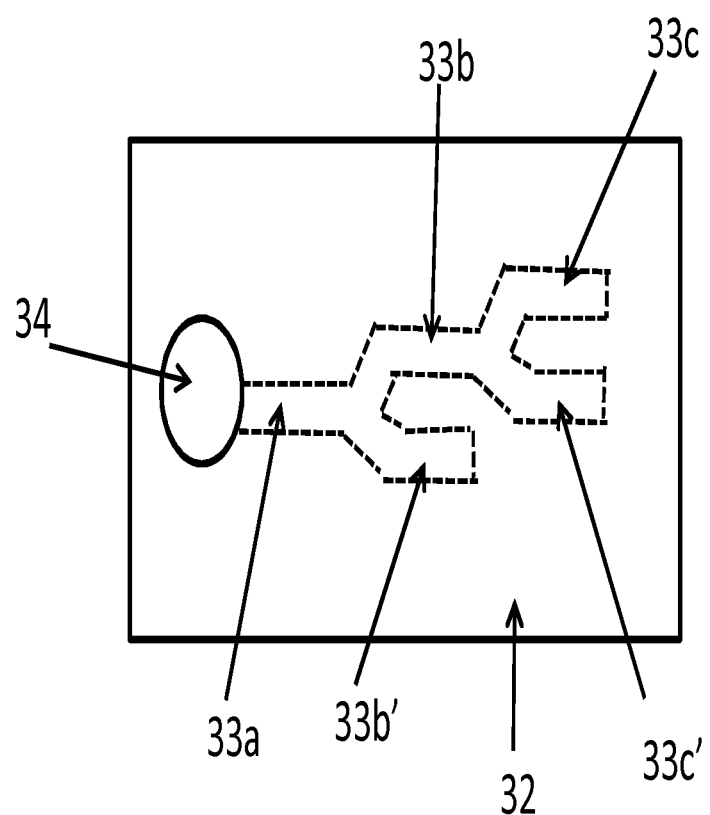
FIG. 4 is a schematic top view of an embodiment of a chamber arrangement with a branched configuration of chamber heights suitable for use in the method and the system of the invention.

The chamber arrangement 32 shown in FIG. 4 comprises a microfluidic chamber with 5 chamber heights for 33*a*, 33*b*, 33*b*', 33*c*, 33*c*' local sample volumes at different chamber heights. The chamber heights 33*a*, 33*b*, 33*b*', 33*c*, 33*c*' are arranged in part in a parallel and in part in a downstream configuration As it can be seen all the chamber heights 33*a*, 33*b*, 33*b*', 33*c*, 33*c*' has a common inlet 34. The chamber heights 33*a*, 33*b*, 33*b*', 33*c*, 33*c*' also have one or more not shown gas escape opening. The chamber height 33*a* is higher than heights of each of different chamber heights 33*b* and 33*b*' downstream to the chamber height 33*a*. The chamber heights 33*b* and 33*b*' immediately downstream to the chamber height 33*a* may be equal or different in height. The chamber height 33*b* has a height which is higher than the heights of each of the chamber heights 33*c* and 33*c*' downstream to the chamber height 33*b*. The chamber heights 33*c* and 33*c*' immediately downstream to the chamber height 33*b* may be equal or different in height.

Figure 5:
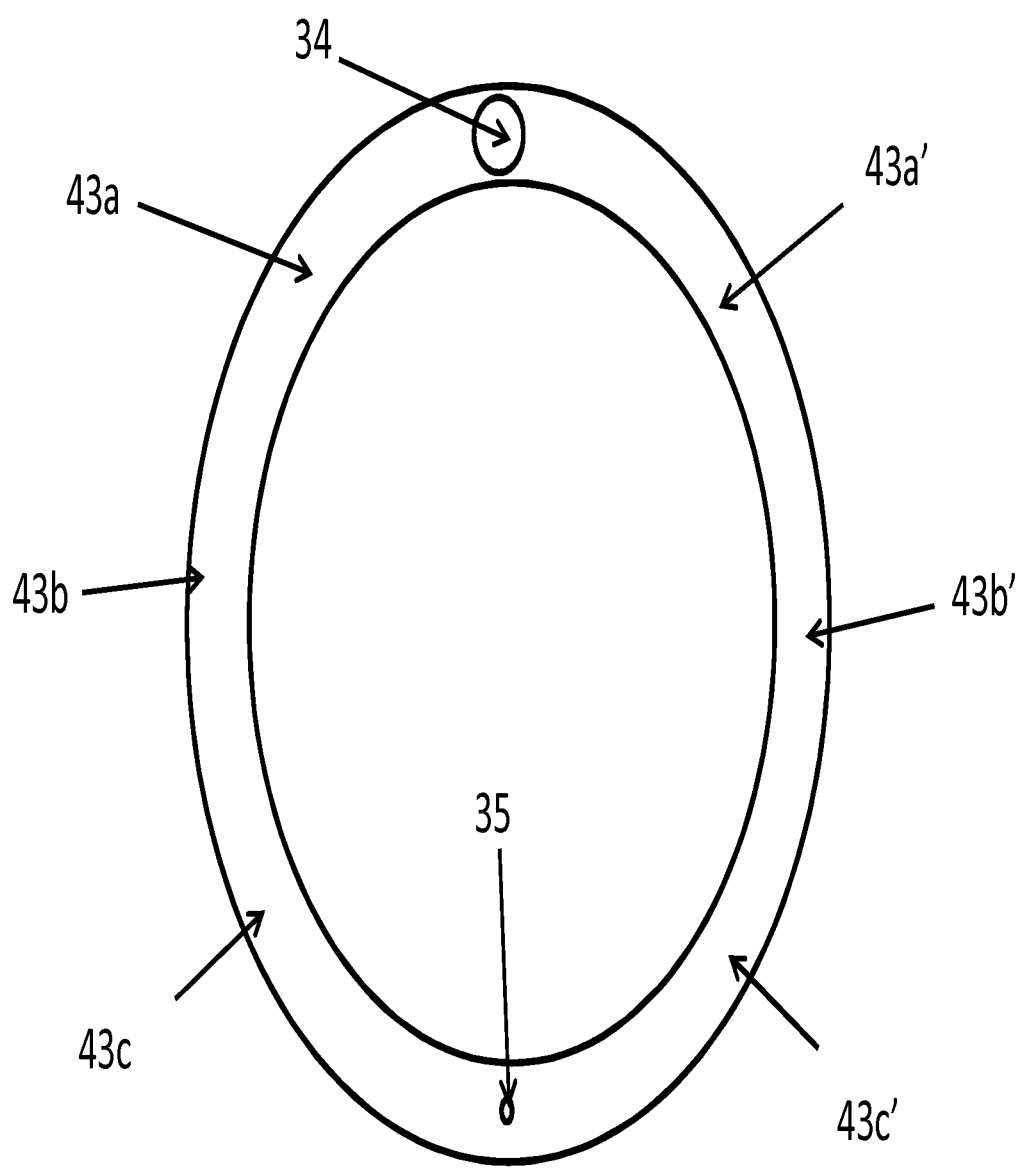
FIG. 5 is a schematic top view of an embodiment of a chamber arrangement where the various local sample volumes at different chamber heights are arranged in a circular configuration.
Figure 6A:
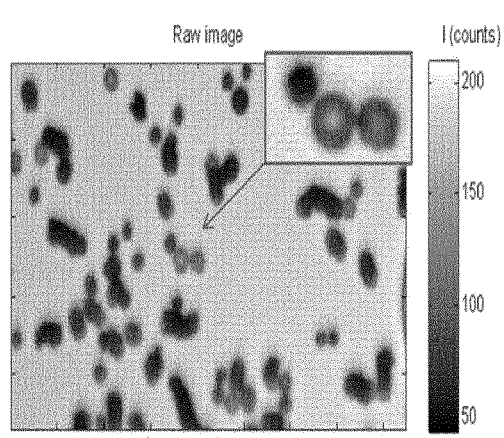
FIG. 6*a* is an image of whole blood in a shallow chamber height imaged at focus using 420 µm back-illuminations The RBCs appears as dark objects due to the strong absorption.
Figure 6B:
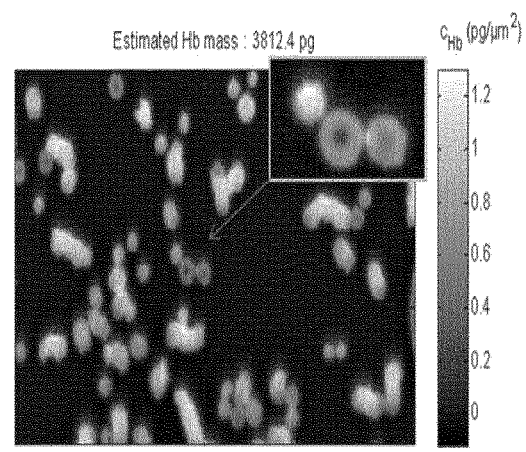
FIG. 6*b* is a Hb mass density map calculated from the image of FIG. 6*a*.
Figure 7:
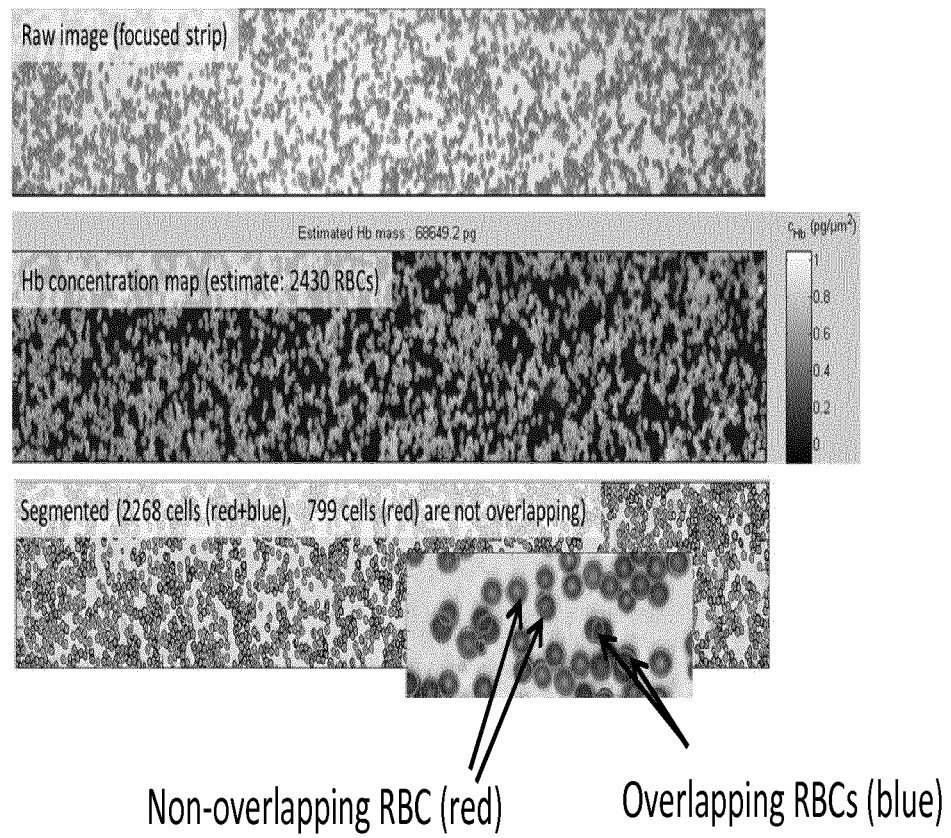
FIG. 7 Top shows an image of a whole blood sample in a shallow chamber (4.0 µm) using 420 µm back-illumination.

The chamber arrangement shown in FIG. 5 comprises a microfluidic chamber which in principle may contain any number of local sample volumes at different chamber heights along its annular extension. The shown embodiment is illustrated with 6 local sample volumes at different chamber heights 43*a*, 44*b*, 43*b*, 43*b*', 43*c*, 43*c*' arranged in an annular configuration with a common inlet 44 and a common gas escape opening 45. The different chamber heights 43*a*, 43*b*, 43*c* have decreasing heights in downstream direction from the inlet 44 to the gas escape opening 45 where for example the chamber height 43*a* has large height, the chamber height 43*b* has medium height and the chamber height 43*c* has a shallow height. In the same way the chamber heights 43*a*', 43*b*', 43*c*' have decreasing heights in downstream direction from the inlet 44 to the gas escape opening 45. The chamber heights 43*a*, 44*b*, 43*b*, 43*b*', 43*c*, 43*c*' may advantageously have pair wise equal heights for providing double test using only one chamber arrangement.

Figure 8:
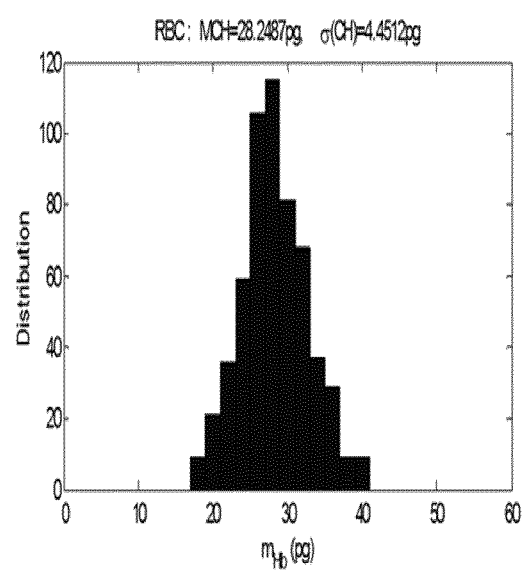
FIG. 8 shows the distribution of corpuscular hemoglobin mass mHb in a whole blood sample. The mean corpuscular hemoglobin (MCH) for this particular blood sample is 28.2 pg.

A shown in FIG. 8 the method and system of the invention may be applied to determine a distribution of corpuscular hemoglobin mass mHb in a whole blood sample. This may be in the form of a histogram as shown. The result of such histogram may for example be used in diagnostic and/or for following a patient's recovery from a disease or similar.

The invention also relates to the following aspects:
1. A method of determining a concentration of a substance in a cell suspension, said method comprising
  flowing said cell suspension into a chamber arrangement performing absorption measurements of n local sample volumes contained at different average chamber heights of said chamber arrangement determining the local substance concentration in said respective local sample volumes based on said respective absorption measurements, generating a substance concentration model comprising local substance concentration as a function of chamber height, and determining the substance concentration as the infinite chamber height substance concentration using said substance concentration model, wherein n is at least 2, such as at least 3, such as at least 4.

2. The method of claim 1, wherein said chamber arrangement is a single chamber device and said cell suspension is supplied to said chamber arrangement to capillary loading said local sample volumes to said chamber heights, preferably said chamber heights are arranged along a common flow path of the chamber arrangement with gradually decreasing heights and preferably comprises at least 3 different chamber heights which differ from each other with at least about 2.5 µm.

3. The method of claim 1 or claim 2, wherein said maximal height of said chamber heights is about 40 µm or less, such as about 30 µm or less, such as about 25 µm or less, such as about 20 µm or less.

4. The method of any one of the preceding claims, wherein said chamber arrangement being at least partially optically transparent for light of at least one preselected wavelength to at least partially allow a light beam of said preselected wavelength passing through the chamber arrangement at said chamber heights, said absorption measurements of local sample volumes contained at said respective chamber heights comprises using a light source emitting light comprising at least said preselected wavelength.

5. The method of any one of the preceding claims, wherein each of said absorption measurements comprises illuminating said local sample volume of the cell suspension at the chamber height from a first side of the chamber arrangement using said light source and recording transmitted light by acquiring at least one image on a second opposite side of the chamber arrangement, wherein the absorption measurements optionally are performed of local sample volumes at two or more of said chamber heights simultaneously.

6. The method of claim 4 or claim 5, wherein said preselected wavelength comprises a wavelength at an isobestic point of the substance, preferably the substance is Hb, and the isobestic point comprises at least one of the wavelengths about 420 µm, about 530 µm and about 570 µm.

7. The method of claim 6, wherein the determination of the local substance concentration in each of said respective local sample volumes comprises image processing the acquired image of the local sample volume, where the substance is Hb the image processing comprises removing interference generated by free plasma Hb and correlating the total normalized light intensity of the acquired image of the chamber height section to a local Hb concentration at the height (z) in question.

8. The method of any one of the preceding claims, wherein the determination of the substance concentration model comprising mapping the local substance concentrations (Lc-substance) of the local sample volumes as a function of the height Lc-substance(z) and calculating a best fitting curve to said mapping and extrapolating said best fitting curve to a height $z \to \infty$ and determining the substance concentration as the substance concentration at the height $Z=\infty$.

9. The method of any one of the preceding claims, wherein the cell suspension is whole blood and the substance is Hb, said method further comprises determining the Mean Corpuscular Hemoglobin (MCH), said method comprising performing at least one absorption measurement at a low chamber heights of about 5 µm or less, and determining the MCH from said absorption measurement at said low chamber height, wherein the low chamber height is from about 2 µm to about 3.5 µm, such as from about 2.5 to about 3 µm.

10. The method of claim 9, wherein the absorption measurement at said low chamber height comprises acquiring at least one image and identifying image areas of a plurality of individual red blood cells and determining the absorbance of said identified areas and correlating the determined absorbance to the MCH, preferably the method comprises counting the number of the plurality of individual red blood cells, determining the average absorbance of a blood cell and correlating the average absorbance of a blood cell to the MCH, preferably the plurality of individual red blood cells are identified as non-overlapping red blood cells.

11. The method of claim 9 or claim 10, wherein the method further comprises determining the concentration of red blood cells cRBC of the blood sample said method comprising correlating the determined Hb concentration to the MCH to thereby determining the cRBC.

12. A system for determining a concentration of a substance in a cell suspension, said system comprising a computer system programmed for generating a substance concentration model comprising local substance concentration as a function of chamber height, and determining the substance concentration as the infinite height substance concentration using the substance concentration model.

13. The system of claim 12, wherein the system comprises a chamber arrangement comprising n different chamber heights configured for being loaded by said cell suspension by flowing, and being at least partially optically transparent for at least one preselected wavelength to at least partially allow a light beam of said preselected wavelength passing through the chamber arrangement at said chamber heights, a light source configured for emitting light comprising at least said preselected wavelength and being arranged to illuminate at least one a local sample volume at one of said n sample heights an image acquisition device configured for acquire images of light passing through said local sample volume wherein said computer system further is programmed for processing images obtained by said image acquisition device of local sample volumes at n different heights to determine the local substance concentration in each of said respective local sample volumes, wherein n is at least 2, such as at least 3, such as at least 4, such as 2-10.

14. The system of claim 13, wherein the maximal chamber heights is less than depth of focus of the image acquisition device and wherein said computer system being programmed to controlling the relative position of said chamber arrangement, said light source and said image acquisition device to control that the depth of focus comprises local sample volumes at said respective chamber heights for acquiring said respective images;

controlling said light source and said image acquisition device for illuminating said local sample volumes and acquisition of images of light transmitted through said local sample volumes at said respective chamber heights;

receiving images obtained by said image acquisition device; and processing said images to determine the substance concentration of said cell suspension.

15. The system of claim 13 or claim 14, wherein said system is configured for determining the Hb concentration in whole blood, at least one of said chamber heights of the chamber arrangement is a low chamber height of about 5 µm or less and the computer system is programmed for performing absorption measurement by acquiring at least one image of a local blood volume at said low chamber height and for determining the MCH from said absorption measurement of said local blood volume at said low chamber height.

16. The system of claim 15, wherein the absorption measurement of said local blood volume at said low chamber height comprises identifying image areas of a plurality of individual red blood cells and determining the absorbance of said identified areas and correlating the determined absorbance to the MCH, preferably the absorption measurement comprises counting the number of the plurality of individual red blood cells, determining the average absorbance of a blood cell and correlating the average absorbance of a blood cell to the MCH.

17. The system of any one of the preceding claims, wherein the said system further is configured for determining the concentration of red blood cells cRBC of the blood sample, said computer system being programmed to determining the concentration of red blood cells cRBC of the blood sample by correlating the determined Hb concentration to the MCH to thereby determining the cRBC.

The invention claimed is:

1. A method of determining a concentration of a substance in a cell suspension, said method comprising the following steps:
    using the results of absorption measurements performed at n local sample volumes contained at different average chamber heights of a chamber arrangement comprising the cell suspension, wherein a local substance concentration in said respective local sample volumes determined based on said respective absorption measurements;
    using a substance concentration model comprising local substance concentration as a function of chamber height, and
    determining the substance concentration as the infinite chamber height substance concentration using said substance concentration model and the determined local substance concentrations, wherein n is at least 2, such as at least 3, such as at least 4,
    wherein said maximal height of said chamber heights is about 40 µm or less, such as about 30 µm or less, such as about 25 µm or less, such as about 20 µm or less,
    wherein said preselected wavelength comprises a wavelength at an isobestic point of the substance, preferably the substance is Hb, and the isobestic point comprises at least one of the wavelengths about 420 nm, about 530 nm and about 570 nm,
    and wherein the determination of the local substance concentration in each of said respective local sample volumes comprises image processing the acquired image of the local sample volume, where the substance is Hb the image processing comprises removing interference generated by free plasma Hb and correlating the total normalized light intensity of the acquired image of the chamber height section to a local Hb concentration at the height (z) in question.

2. The method of claim 1, wherein said chamber arrangement is a single chamber device and said cell suspension is supplied to said chamber arrangement to capillary loading said local sample volumes to said chamber heights, preferably said chamber heights are arranged along a common flow path of the chamber arrangement with gradually decreasing heights and preferably comprises at least 3 different chamber heights which differ from each other with at least about 2.5 µm.

3. The method of claim 1, wherein each of said absorption measurements comprises illuminating said local sample volume of the cell suspension at the chamber height from a first side of the chamber arrangement using said light source and recording transmitted light by acquiring at least one image on a second opposite side of the chamber arrangement, wherein the absorption measurements optionally are performed of local sample volumes at two or more of said chamber heights simultaneously.

4. A method of determining a concentration of a substance in a cell suspension, said method comprising the following steps:
    using the results of absorption measurements performed at n local sample volumes contained at different average chamber heights of a chamber arrangement comprising the cell suspension, wherein a local substance concentration in said respective local sample volumes determined based on said respective absorption measurements;
    using a substance concentration model comprising local substance concentration as a function of chamber height, and
    determining the substance concentration as the infinite chamber height substance concentration using said substance concentration model and the determined local substance concentrations, wherein n is at least 2, such as at least 3, such as at least 4,
    wherein the determination of the substance concentration model comprising mapping the local substance concentrations (Lc-substance) of the local sample volumes as a function of the height Lc-substance(z) and calculating a best fitting curve to said mapping and extrapolating said best fitting curve to a height $z \rightarrow \infty$ and determining the substance concentration as the substance concentration at the height $Z=\infty$.

5. The method of claim 1, wherein the cell suspension is whole blood and the substance is Hb, said method further comprises determining the Mean Corpuscular Hemoglobin (MCH), said method comprising performing at least one absorption measurement at a low chamber heights of about 5 µm or less, and determining the from said absorption measurement at said low chamber height, wherein the low chamber height is from about 2 µm to about 3.5 µm, such as from about 2.5 to about 3 µm.

6. A method of determining a concentration of a substance in a cell suspension, said method comprising the following steps:
    using the results of absorption measurements performed at n local sample volumes contained at different average chamber heights of a chamber arrangement comprising the cell suspension, wherein a local substance concentration in said respective local sample volumes determined based on said respective absorption measurements;
    using a substance concentration model comprising local substance concentration as a function of chamber height, and
    determining the substance concentration as the infinite chamber height substance concentration using said substance concentration model and the determined local substance concentrations, wherein n is at least 2, such as at least 3, such as at least 4;

wherein the cell suspension is whole blood and the substance is Hb, said method further comprises determining the Mean Corpuscular Hemoglobin (MCH), said method comprising performing at least one absorption measurement at a low chamber heights of about 5 µm or less, and determining the from said absorption measurement at said low chamber height, wherein the low chamber height is from about 2 µto about 3.5 µm, such as from about 2.5 to about 3 µm, wherein the absorption measurement at said low chamber height comprises acquiring at least one image and identifying image areas of a plurality of individual red blood cells and determining the absorbance of said identified areas and correlating the determined absorbance to the MCH, preferably the method comprises counting the number of the plurality of individual red blood cells, determining the average absorbance of a blood cell and correlating the average absorbance of a blood cell to the MCH, preferably the plurality of individual red blood cells are identified as non-overlapping red blood cells.

7. The method of claim 1, wherein the method further comprises at least one of the following steps:
    flowing said cell suspension into the chamber arrangement;
    performing absorption measurements of the n local sample volumes contained at different average chamber heights of said chamber arrangement.

8. A system for determining a concentration of a substance in a cell suspension, said system comprising a computer system programmed for causing the system to execute the method of claim 1.

9. A system for determining a concentration of a substance in a cell suspension, said system comprising a computer system programmed for causing the system to execute a method of determining a concentration of a substance in a cell suspension, said method comprising the following steps:
    using the results of absorption measurements performed at n local sample volumes contained at different average chamber heights of a chamber arrangement comprising the cell suspension, wherein a local substance concentration in said respective local sample volumes determined based on said respective absorption measurements;
    using a substance concentration model comprising local substance concentration as a function of chamber height, and
    determining the substance concentration as the infinite chamber height substance concentration using said substance concentration model and the determined local substance concentrations, wherein n is at least 2, such as at least 3, such as at least 4, wherein the system further comprises:
        a chamber arrangement comprising n different chamber heights configured for being loaded by said cell suspension by flowing, and being at least partially optically transparent for at least one preselected wavelength to at least partially allow a light beam of said preselected wavelength passing through the chamber arrangement at said chamber heights,
        a light source configured for emitting light comprising at least said preselected wavelength and being arranged to illuminate at least one a local sample volume at one of said n sample heights
        an image acquisition device configured for acquire images of light passing through said local sample volume wherein said computer system further is programmed for processing images obtained by said image acquisition device of local sample volumes at n different heights to determine the local substance concentration in each of said respective local sample volumes, wherein n is at least 2, such as at least 3, such as at least 4, such as 2-10.

10. The system of claim 9, wherein the maximal chamber heights is less than depth of focus of the image acquisition device and wherein said computer system being programmed to
    controlling the relative position of said chamber arrangement, said light source and said image acquisition device to control that the depth of focus comprises local sample volumes at said respective chamber heights for acquiring said respective images;
    controlling said light source and said image acquisition device for illuminating said local sample volumes and acquisition of images of light transmitted through said local sample volumes at said respective chamber heights;
    receiving images obtained by said image acquisition device; and
    processing said images to determine the substance concentration of said cell suspension.

11. The system of claim 9, wherein said system is configured for determining the Hb concentration in whole blood, at least one of said chamber heights of the chamber arrangement is a low chamber height of about 5 µm or less and the computer system is programmed for performing absorption measurement by acquiring at least one image of a local blood volume at said low chamber height and for determining the MCH from said absorption measurement of said local blood volume at said low chamber height.

12. The method of claim 4, wherein the method further comprises determining cRBC based on the determined Hb concentration and the determined MCH.

* * * * *